US00PP28373P3

(12) United States Plant Patent
Shock et al.

(10) Patent No.: US PP28,373 P3
(45) Date of Patent: Sep. 12, 2017

(54) *STEVIA* PLANT NAMED 'SW 129'

(50) Latin Name: *Stevia rebaudiana*
Varietal Denomination: SW 129

(71) Applicant: S&W Seed Company, Fresno, CA (US)

(72) Inventors: Clinton C. Shock, Ontario, OR (US); Cheryl A. Parris, Ontario, OR (US)

(73) Assignee: S&W Seed Company, Hanford, CA (US)

( * ) Notice: Subject to any disclaimer, the term of this patent is extended or adjusted under 35 U.S.C. 154(b) by 13 days.

(21) Appl. No.: 14/757,095

(22) Filed: Nov. 17, 2015

(65) Prior Publication Data

US 2017/0142885 P1 May 18, 2017

(51) Int. Cl.
*A01H 5/00* (2006.01)

(52) U.S. Cl.
USPC ..... Plt./258

(58) Field of Classification Search
USPC ..... Plt./258, 263.1
See application file for complete search history.

(56) References Cited

U.S. PATENT DOCUMENTS

| | | | |
|---|---|---|---|
| PP10,562 | P | 8/1998 | Sys et al. |
| PP10,563 | P | 8/1998 | Brandle et al. |
| PP10,564 | P | 8/1998 | Marsolais et al. |
| 6,031,157 | A | 2/2000 | Morita et al. |
| 6,080,561 | A | 6/2000 | Morita et al. |
| 6,255,557 | B1 | 7/2001 | Brandle |
| 7,862,845 | B2 | 1/2011 | Magomet et al. |
| 7,884,265 | B2 | 2/2011 | Morita et al. |
| PP22,593 | P3 | 3/2012 | Garnighian |
| PP23,164 | P3 | 11/2012 | Britos |
| PP23,728 | P3 | 7/2013 | Britos |
| 2009/0214753 | A1 | 8/2009 | Morita et al. |
| 2011/0023192 | A1 | 1/2011 | Morita et al. |
| 2011/0195169 | A1 | 8/2011 | Markosyan et al. |
| 2011/0271413 | P1 | 11/2011 | Garnighian |
| 2012/0058247 | A1 | 3/2012 | Shi |
| 2012/0090062 | P1 | 4/2012 | Alvarez |
| 2013/0347140 | A1 | 12/2013 | Wang |
| 2016/0057955 | A1 | 3/2016 | Li et al. |
| 2016/0057965 | A1 | 3/2016 | Li et al. |
| 2016/0165777 | P1 | 6/2016 | Warner et al. |
| 2016/0165778 | P1 | 6/2016 | Warner et al. |
| 2016/0165779 | P1 | 6/2016 | Warner et al. |

OTHER PUBLICATIONS

Ali et al., Biochemical Investigation During Different Stages of in Vitro Propagation of *Stevia rebaudiana,* Pak. J. Bot., 42(4): 2827-2837 (2010).

Henderson, Jr. and Berry, Isocratic *Stevia* Sweetener Analysis using Selective Zorbax Columns: Application Note—Food, www.agilent.com/chem, Agilent Technologies, Inc. 5990-3933EN (Apr. 30, 2009), 6 pages total.

Ahmed et al., An Efficient Method for in vitro Clonal Propagation of a Newly Introduced Sweetener Plant (*Stevia rebaudiana* Bertoni.) in Bangladesh, American-Eurasian Journal of Scientific Research 2(2):121-125 (2007).

Akita et al., Mass propagation of shoots of *Stevia rebaudiana* using large scale bioreactor, Plant Cell Reports 13:180-183 (1994).

Anbazhagan et al., In vitro production of *Stevia rebaudiana* Bertoni, Emir. J. Food Agric. 22(3):216-222 (2010).

Midmore and Rank, A new rural industry—*Stevia*—to replace imported chemical sweeteners, Rural Industries Research and Development Corporation, Publication No. W02/022 (Aug. 2002), 25 pages total.

Brandle et al., *Stevia rebaudiana*: Its agricultural, biological, and chemical properties, Can. J. Plant Sci. 78:527-536 (1998).

Brandle and Telmer et al., Steviol glycoside biosynthesis, Phytochemistry 68:1855-1863 (2007).

Dacome et al., Sweet diterpenic glycosides balance of a new cultivar of *Stevia rebaudiana* (Bert.) Bertoni: Isolation and quantitative distribution by chromatographic, spectroscopic, and electrophoretic methods, Process Biochemistry 10:3587-3594 (2005).

Debnath, Clonal propagation and antimicrobial activity of an endemic medicinal plant *Stevia rebaudiana,* Journal of Medicinal Plants Research 2(2):045-051 (2008).

Goettemoeller and Ching, Seed Germination in *Stevia rebaudiana,* J. Janick (ed), ASHS Press (1999), pp. 510-511.

Jena et al., Effect of phytoregulators on in vitro mass propagation of *Stevia rebaudiana* Bertoni, International Journal of Integrative Biology, 8(1):56-59 (2009).

Kolb et al., Analysis of Sweet Diterpene Glycosides from *Stevia rebaudiana*: Improved HPLC Method, J. Agric. Food Chem. 49:4538-4541 (2001).

Madan et al., *Stevia rebaudiana* Bertoni—A Review, Indian Journal of Natural Products and Resources 1(3):267-286 (2010).

Reick et al., Improved HPLC method for the evaluation of the major steviol glycosides in leaves of *Stevia rebaudiana,* Eur. Food Res. Technology 231:581-588 (2010).

Sharma et al., Chemistry and in vivo profile of ent-kaurene glycosides of *Stevia rebaudiana* Bertoni—An overview, Natural Product Radiance 8(2):181-189 (2009).

(Continued)

*Primary Examiner* — Susan McCormick Ewoldt
(74) *Attorney, Agent, or Firm* — Karen Canaan; CanaanLaw, P.C.

(57) ABSTRACT

A new and distinct *Stevia rebaudiana* plant named 'SW 129' is described. The new variety is distinguished from other *Stevia* varieties by high plant vigor; high plant yield; late flowering; excellent sweet leaf taste with very low bitterness and aftertaste; and leaves having a high rebaudioside A, a high percentage of rebaudioside A to total steviol glycosides, and a high ratio of rebaudioside A content to stevioside content.

4 Drawing Sheets

(56) References Cited

OTHER PUBLICATIONS

Shatnawi et al., Clonal propagation and cryogenic storage of the medicinal plant *Stevia rebaudiana,* Spanish Journal of Agricultural Research 9(1):213-220 (2011).
Shimadzu, Analysis of Steviol Glycosides in *Stevia* Extract, Shimadzu Corporation Application News, No. L439 (2012), 2 pages total.
Shock, Experimental Cultivation of Rebaudi's *Stevia* in California, University of California Davis, Agronomy Progress Report No. 122 (Apr. 1982), 9 pages total.
Shock, Rebaudi's *Stevia*: natural noncaloric sweeteners, California Agriculture 36(9) and (10), University of California Davis, Division of Agricultural Sciences Reports of Progress in Research (Sep.-Oct. 1982).
Tavarini and Agnelini, *Stevia rebaudiana* Bertoni as a source of bioactive compounds: the effect of harvest time, experimental site and crop age on steviol glycoside content and antioxidant properties, J. Sci. Food. Agric. 93:2121-2129 (2013).
Taware et al., Comparative studies of in vitro and in vivo grown plants and callus of *Stevia rebaudiana* (Bertoni), International Journal of Integrative Biology 9(1):10-15 (2010).
Yadav et al., A review on the improvement of *Stevia* [*Stevia rebaudiana* (Bertoni)], Can. J. Plant Sci. 91:1-27 (2011).
International Search Report and Written Opinion for commonly owned PCT/US2015/060925 dated Jan. 29, 2016.
International Search Report and Written Opinion for commonly owned PCT/US2015/061185 dated Feb. 1, 2016.
S&W Press Release for SW 107 Varietal dated Dec. 1, 2014 (The SW 107 Varietal was filed as Plant U.S. Appl. No. 14/544,136, filed Nov. 30, 2014).

*STEVIA* PLANT NAMED 'SW 129'

Genus and species: *Stevia rebaudiana.*
Variety denomination: 'SW 129'.

BACKGROUND OF THE INVENTION

*Stevia rebaudiana* is a plant species in the sunflower (Asteraceae) family, which has naturally sweet leaves. The active compounds that impart the sweet flavor to *stevia* leaves are steviol glycosides. The most common steviol glycosides are stevioside and rebaudioside A, both of which have up to 250 to 400 times the sweetness of sugar. Stevioside tends to be more prevalent in unimproved lines of *stevia* leaves than rebaudioside A. The development of new varieties of *Stevia rebaudiana* with higher levels of rebaudioside A than stevioside is desirable for use as a sugar substitute.

The present invention relates to a new and distinct variety of *Stevia rebaudiana*, the 'SW 129' line, which has very sweet leaves with high levels of steviol glycosides and very low bitterness and aftertaste, excellent overwintering, high plant vigor, high leaf yield, and late flowering.

The 'SW 129' line was selected on Jun. 9, 2013, as a single plant in a population of recurrently selected *Stevia rebaudiana*, the population of which was originally grown from seed in an outdoor field in Chowchilla, Calif., USA, under natural lighting. The parentage of the 'SW 129' line is not known and population from which the 'SW 129' line was derived has no patented parental lineage. The plant that produced the 'SW 129' line was selected from its population based upon the following characteristics, which were measured and/or observed from Jun. 9, 2013, to October 2014.

Plant Vigor: The 'SW 129' line was found on Jun. 9, 2013, to have greater growth and survival in comparison to the majority of the plant population from which the line was derived.

Timing of Flowering: The 'SW 129' line was found in October 2013 to have later flowering (an advantage for leaf production) in comparison to the majority of the plant population from which the line was derived.

Leaf Taste: The leaves of the 'SW 129' line were found in August 2013 to have an excellent sweet taste in comparison to a majority of the plant population from which the line was derived and very little bitterness and aftertaste in comparison to most *stevia* varieties.

Rebaudioside A content: In 2014, the leaves of the 'SW 129' line were found to have a high percentage of rebaudioside A at 13.58% (Table 1), with 77.50% of the steviol glycosides in the leaves of the 'SW 129' line being attributed to rebaudioside A.

Ratio of rebaudioside A to stevioside content: The ratio of rebaudioside A to stevioside in the leaves of the 'SW 129' line was found to be high at 6.41 (Table 1).

Upon initial selection of the single plant in Chowchilla, Calif., the 'SW 129' line was asexually reproduced from rooted cuttings starting Jun. 11, 2013, in Ontario, Oreg. Plant yield and leaf quality of the 'SW 129' line were confirmed in April through October 2014 through replicated yield trials in the following three locations in the USA: Yuma, Ariz.; Indio, Calif.; and Ontario Oreg. At each of the three locations, the performance of the 'SW 129' line grown from cuttings was compared to seedlings of the 'Candy' line (Genesis Seed Ltd., Ashalin, Israel; not patented) grown from bulk commercial seed ("the check variety"). Table 1 compares various characteristics of an average sampling of leaves of the 'SW 129' line with an average sampling of leaves of the check variety.

TABLE 1

| | SW 129 | Check Variety ('Candy') |
|---|---|---|
| Percentage of Rebaudioside A | 13.58% | 6.85% |
| Percentage of Stevioside | 2.12% | 6.42% |
| Percentage of total Steviol Glycosides | 17.50% | 14.71% |
| Ratio of Rebaudioside A:Stevioside | 6.41 | 1.11 |
| Percentage of Rebaudioside A to total Steviol Glycosides | 77.6% | 46.8% |

The data in the foregoing table shows that in comparison to the check variety, the 'SW 129' line contained more rebaudioside A (13.58% vs. 6.85%); less stevioside (2.12% vs. 6.42%); more total steviol glycosides (17.50% vs. 14.71%); a higher rebaudioside A to stevioside ratio (6.41 vs. 1.11); and a higher percentage of rebaudioside A to total steviol glycosides (77.6% vs. 46.8%). In addition to the foregoing, the 'SW 129' line also produced 22% more leaf yield than the check variety with the 'SW 129' line producing 5178 lb. of leaf per acre per year versus 4232 lb. of leaf per acre per year for the check variety at Ontario, Oreg. Leaf yield results were averaged over two harvest strategies (one or two cuttings per year). The higher yield of the 'SW 129' line over the check variety in the Ontario, Oreg. location was due in part to low stand loss from *Fusarium* and other root diseases that reduced plant stand of the check variety. Overall leaf yield was higher in Ontario, Oreg. than in the hotter, drier climates of Yuma, Ariz. and Indio, Calif.

BRIEF SUMMARY OF THE INVENTION

The following characteristics of the new 'SW 129' line have been repeatedly observed and can be used to distinguish the 'SW 129' line as a new and distinct cultivar of a *Stevia* plant:

1. High plant vigor;
2. High plant yield;
3. Late flowering;
4. Excellent sweet flavor to the leaves with very little bitterness and aftertaste;
5. Leaves having a rebaudioside A content of over 13%;
6. Leaves having a stevioside content of approximately 2%;
7. Leaves having a ratio of rebaudioside A to stevioside of 6.41;
8. Leaves having a total steviol glycoside content of approximately 17.50%;
9. Leaves having a percentage of rebaudioside A to total steviol glycosides of approximately 77.6%; and
10. Over 5000 lb. of leaf per acre per year.

BRIEF DESCRIPTION OF THE DRAWINGS

The accompanying photographs show, as nearly true as is possible in color illustrations of this type, typical flower and foliage characteristics of the 'SW 129' line. The plants depicted in the accompanying photographs are approximately one year old.

DETAILED BOTANICAL DESCRIPTION

Figure 1:
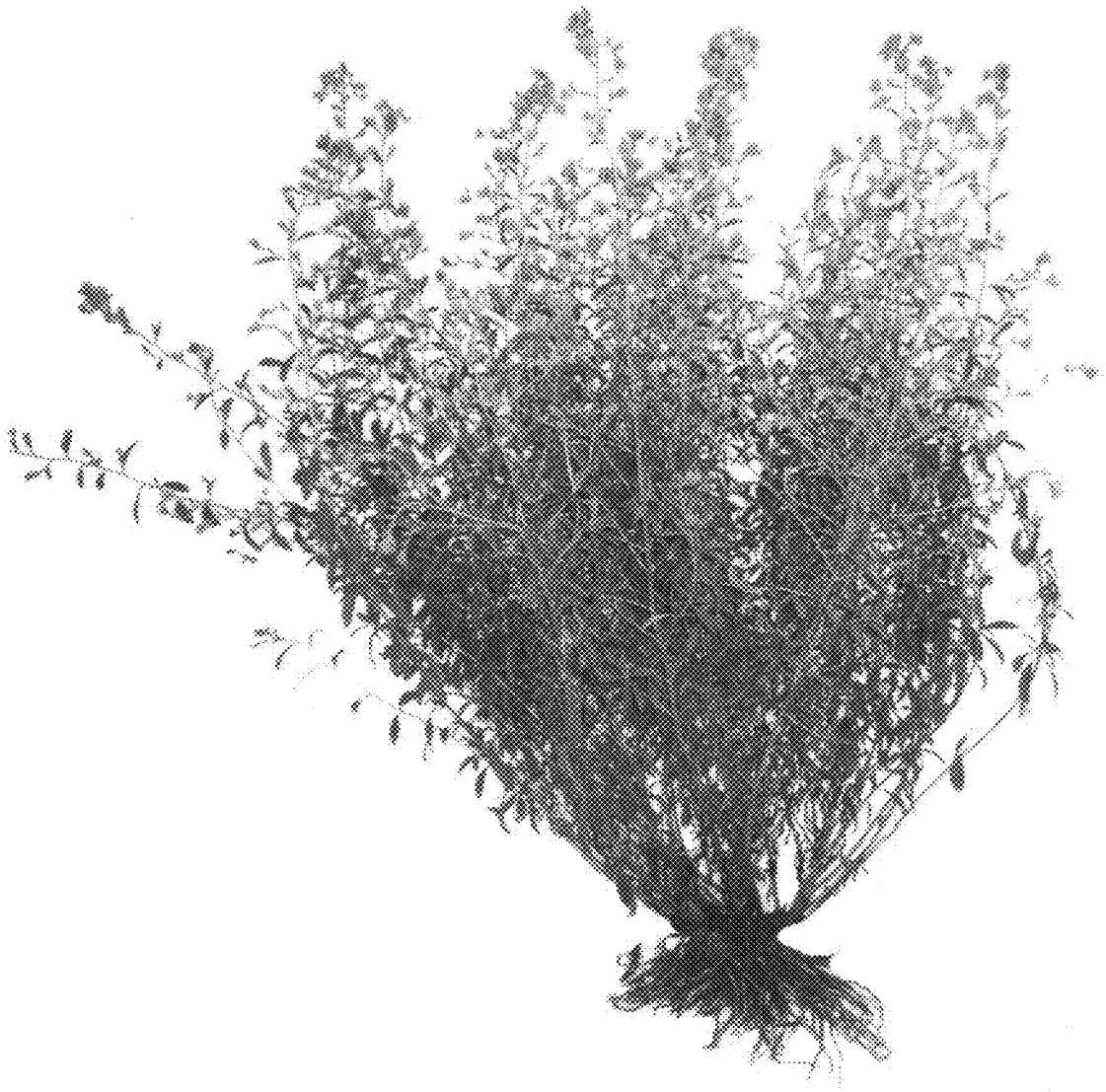
FIG. 1 depicts a color photograph of a fully mature 'SW 129' *Stevia* plant from roots to top of the plant near the end of the plant's first growing season.

Following is a detailed botanical description of a new and distinct variety of a *Stevia* plant known as 'SW 129'. Plant observations were made on Aug. 24, 2014, on mature one year old plants grown in a field in Ontario, Oreg. in natural light. The 'SW 129' line has not been observed under all possible environmental conditions. Where characteristics, such as dimensions, sizes, colors, and other such characteristics are given, it is to be understood that such characteristics are approximations or averages and that such approximations are not intended to be limiting. It is also to be understood that the phenotype of the variety may be altered by changes with environment, such as season, temperature, light quality, light intensity, day length, cultural conditions, and the like. Color notations are based on *The Royal Horticultural Society Colour Chart*, The Royal Horticultural Society, London, 2007.

Where appropriate, the following description makes reference to commonly owned *stevia* line 'SW 107', which is disclosed in co-pending Plant patent application Ser. No. 14/544,136, filed on Nov. 14, 2014 (now U.S. Plant Pat. No. 27,815). The 'SW 129' line differs from the 'SW 107' line is many respects, including without limitation, the percentage of rebaudioside A (10.39% for 'SW 107' versus 13.58% for 'SW 129'); the percentage of stevioside (4.76% for 'SW 107' versus 2.12% for 'SW 129'); percentage of total steviol glycosides (16.89% for 'SW 107' versus 17.50% for 'SW 129'); and number of leaf harvest per acre per year (4500 for 'SW 107' versus 5000 for 'SW 129').

Botanical classification: *Stevia rebaudiana* cultivar 'SW 129'.

Parentage: *Stevia* plants (unpatented) grown from seeds (unpatented) in Chowchilla, Calif. by Clinton C. Shock.

Plant (description based on FIG. 1):
- *Type*.—Perennial in climates with mild winter temperatures.
- *Form and habit*.—Multiple branching bush.
- *Height* (*from top of soil*).—32 cm.
- *Width* (*including flowers*).—28 cm.
- *Number of nodes on main stem*.—Varies. After initial growth, the number of principle stems proliferates.
- *Number of basal buds*.—Fewer basal buds developed during the growing season, compared with 'SW 107'.
- *Stooling*.—Less stooling was initiated during the growing season, compared with 'SW 107'.
- *Harvest cycle*.—Summer and fall or fall.
- *Root initiation*.—8 days.

Figure 2:
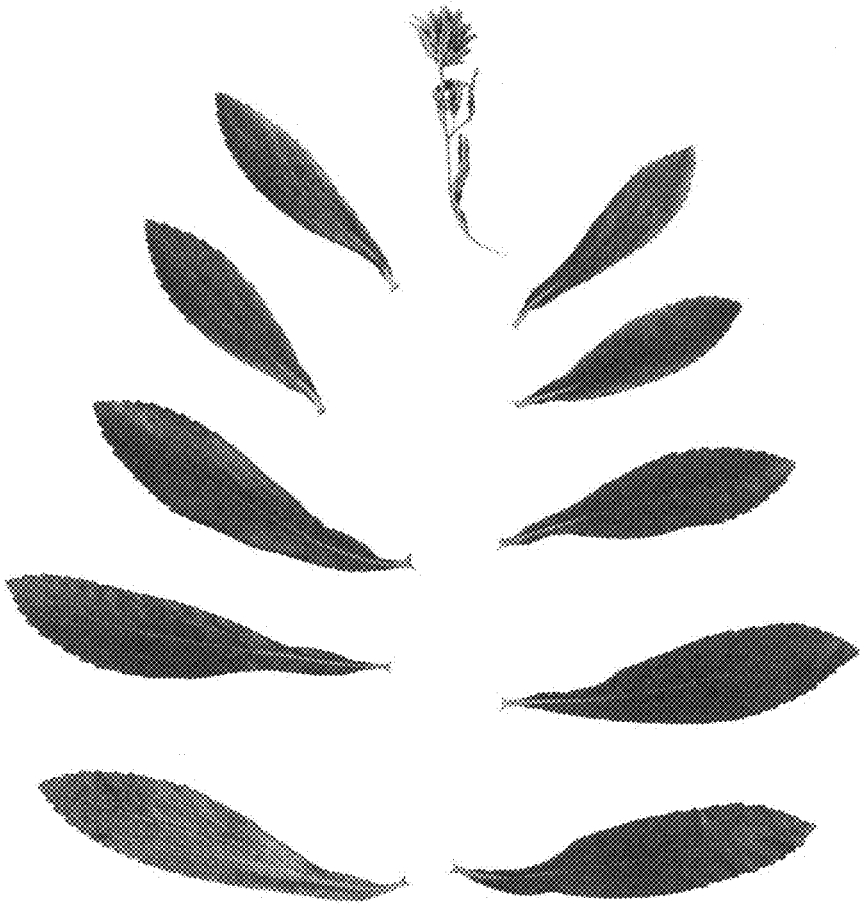
FIG. 2 depicts a color photograph of 'SW 129' leaves.
Figure 3:
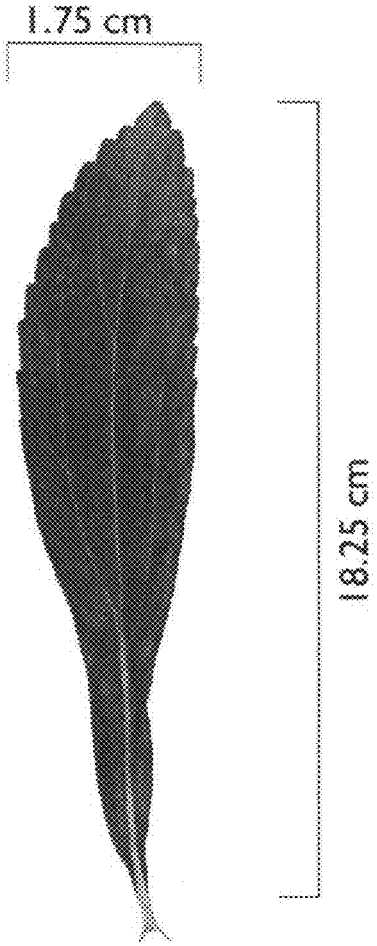
FIG. 3 depicts a color photograph of an 'SW 129' leaf, including the shape and dimensions.

Leaves (description based on FIGS. 2 and 3):
- *Length*.—5.0 cm-10 cm.
- *Width*.—1.0 cm-3.0 cm.
- *Arrangement*.—Opposite.
- *Shape*.—Lanceolate.
- *Apex descriptor*.—Acute.
- *Base descriptor*.—Cuneate.
- *Margin descriptor*.—Serrate.
- *Venation pattern*.—Longitudinal.
- *Color, mature foliage*.—Upper surface. RHS137C. Lower surface. RHS137C.
- *Color, veins*.—RHS 139C.
- *Texture, mature foliage*.—Upper surface. Slight pubescence. Lower surface. Moderate pubescence.
- *Petiole length*.—~0.6 cm.
- *Petiole diameter*.—~0.3 cm.
- *Petiole texture*.—Upper surface: Slight pubescence. Lower surface: Moderate pubescence.
- *Pubescence color*.—Upper surface. RHS 139C. Lower surface. RHS 139C.
- *Stevioside content*.—2.12%.
- *Rebaudioside A content*.—13.58%.
- *Rebaudioside A as a percentage of total steviol glycosides*.—77.6%.
- *Ratio of rebaudioside A to stevioside*.—6.41.
- *Total steviol glycosides*.—17.50%.
- *Leaf harvest period*.—Summer plus fall or fall in Oregon, California, and Arizona.

Stem:
- *Length* (*excluding inflorescence*).—Varies to 32 cm.
- *Diameter*.—Varies to 4.0 cm.
- *Texture*.—Pubescent.
- *Color*.—RHS 145B.

Figure 4:
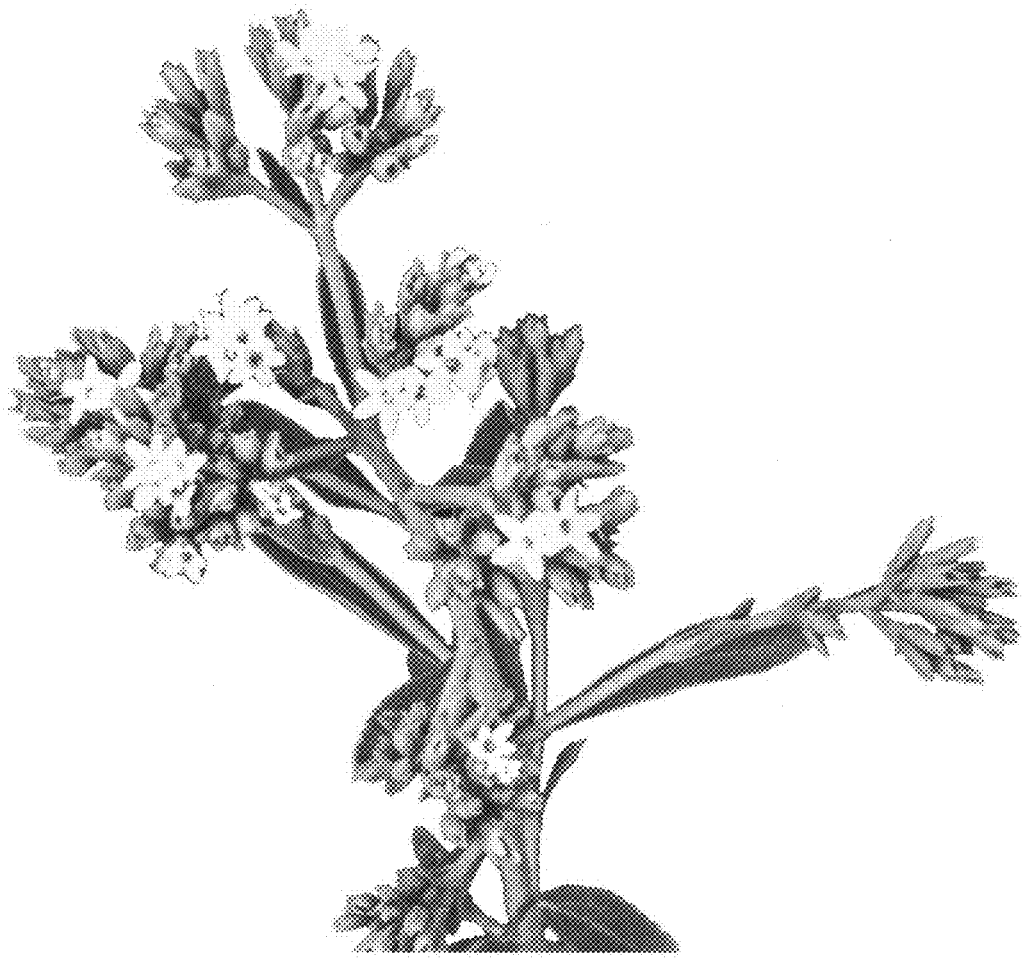
FIG. 4 depicts a color photograph of the flowers of an 'SW 129' *Stevia* plant.

Flowers (description based on FIG. 4):
- *Inflorescence type*.—Panicle.
- *Petal color*.—RHS N155D.
- *Petal length*.—~0.6 cm.
- *Petal width*.—~0.1 cm.
- *Bloom period*.—October to November at Ontario, Oreg.
- *Arrangement*.—Composite.
- *Shape*.—Cluster.
- *Fragrance*.—None.
- *Number of flowers per capitulum*.—5.
- *Average number of petals per flower*.—Five petals fused together in a sympetulous configuration.

Peduncle:
- *Color*.—RHS 145B.
- *Diameter*.—~0.15 cm.
- *Aspect*.—Perpendicular.
- *Texture*.—Pubescent.

Pedicles:
- *Color*.—RHS 145B.
- *Diameter*.—~0.03 cm.
- *Aspect*.—45 degrees.
- *Texture*.—Pubescent.

Disc florets:
- *Arrangement*.—Radially symmetrical.
- *Shape*.—Tubular.

Phyllaries:
- *Quantity*.—5.
- *Length*.—~0.7 cm.
- *Width*.—~0.15 cm.
- *Shape*.—Lanceolate.
- *Apex*.—Acute.
- *Base*.—Fused.
- *Margin*.—Overlapping.
- *Color*.—RHS 145B.

Reproductive organs:
- *Androecium*.—Stamen quantity. 5. Anther length. ~0.4 cm. Anther color. RHS 199A.
- *Gynoecium*.—Pistil length. ~0.8 cm. Style color. RHS N155B. Stigma color. RHS N155B.

Fruit and seed set:
- *Flowering*.—October to November, which is later than most *stevia* lines, which flower from mid-to-late September.
- *Seeds*.—Small black achene with pappus attached typical of *Stevia rebaudiana*.

Cold hardiness: Hardy to 23° F. (−5° C.) at Ontario, Oreg.

Heat tolerance: Hardy to a monthly average maximum temperature of 107-108° F. (42° C.) at Yuma, Ariz. and Indio, Calif.

We claim:

1. A new and distinct cultivar of *Stevia* plant named 'SW 129' as substantially shown and described herein.

* * * * *